United States Patent [19]

Contos

[11] Patent Number: 4,888,359

[45] Date of Patent: Dec. 19, 1989

[54] ANALGESIC AND ANTIINFLAMMATORY PHARMACEUTICAL COMPOSITION CONTAINING A NAPHTHYL-ACETIC ACID DERIVATIVE

[75] Inventor: Simos Contos, Milan, Italy

[73] Assignee: Istituto Biochimico Sperimentale Ibis S.P.A., Florence, Italy

[21] Appl. No.: 352,631

[22] Filed: May 12, 1989

Related U.S. Application Data

[62] Division of Ser. No. 182,932, Apr. 18, 1988, abandoned.

[30] Foreign Application Priority Data

Apr. 23, 1987 [IT] Italy ................................ 20227 A/87

[51] Int. Cl.$^4$ .............................................. A61K 31/19
[52] U.S. Cl. ..................................... 514/569; 562/492
[58] Field of Search .......................... 562/492; 514/569

[56] References Cited

PUBLICATIONS

Chiti et al., *Chemical Abstracts*, vol. 94, No. 20397d (1981).

Primary Examiner—Bruce Gray
Attorney, Agent, or Firm—Walter H. Schneider

[57] ABSTRACT

α-methyl-α-(3,4-dihydro-1-naphthyl)acetic acid, i.e. dinaproic acid, has such valuable analgesic and antiinflammatory activities, as to be useful in human therapy.

1 Claim, No Drawings

ANALGESIC AND ANTIINFLAMMATORY PHARMACEUTICAL COMPOSITION CONTAINING A NAPHTHYL-ACETIC ACID DERIVATIVE

This application is a division of application Ser. No. 182,932 filed Apr. 18, 1988.

The present invention relates to pharmaceutical compositions having analgesic-antiinflammatory activity, containing dinaproic acid as the active ingredient, and to the use of dinaproic acid for the preparation of analgesic and antiinflammatory medicaments.

Dinaproic acid, i.e. α-methyl-α-(3,4-dihydro-1-naphthyl)acetic acid of formula I

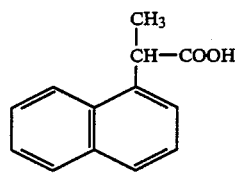

has been described in J. Chem. Soc. 2799–2805, 1969.

Italian patent n. 1.100.784 discloses pharmaceutical compositions having choleretic activity, containing dinaproic acid as the active ingredient.

Choleretic activity is known to be in no way related to analgesic and antiinflammatory activities, which compound I surprisingly proved to possess. Particularly, dinaproic acid was found to have, in usual pharmacologic tests, an activity comparable or higher than that of already known, widely used drugs, such as ibuprofen and acemetacin.

The results obtained from Randall and Selitto test (Arch. Int. Pharm. CX1, 409, 1957), carried out on albino male rats weighing about 120–150 g, fasted for 14–16 hours, are reported hereinbelow.

The rats were previously reparted in several groups and marked, since each rat was the control for itself, during the test.

0.1 ml of a yeast suspension was injected in the plantar area of the right rear paw of each rat, then the animals were orally administered with the vehicle of the compound ($H_2O$ or 5% gum arabic) in a volume of 5 ml/kg.

The test compounds were administered immediately after the injection of the phlogistic agent (with the same procedure used for controls).

Each compound was administered per os in a volume of 5 ml/kg.

The pain reaction threshold was determined 1-3-5 hours after the treatment.

Said threshold was determined placing the animal's paw on a teflon plateform of a Basile analgesimeter, and operating the engine of the device, thereby gradually increasing the weight strength applied on the paw, by means of the displacement of a weight on an endless screw.

When the rat showed evident pain manifestations, the engine was arrested and the value on the graduated scale was read. Said value (in grams) is called "pain reaction threshold".

The normal paw and the treated paw volumes were measured by a plethysmograph 3 hours after the treatment, thereby obtaining information also about a possible anti-oedema activity.

Analgesia was expressed as the percentage increase of the pain threshold measured at each time interval after the treatment.

An approximative ED50 may be determined from the comparison from treated and control animals, by reporting the data on a semi-logarithmic probability chart.

The results obtained by administered 100 mg/kg of dinaproic acid or ibuprofen, are reported hereinbelow.

| Test n. | Normal left paw | Inflammated right paw |
|---|---|---|
| RANDALL-SELITTO READING 1 HOUR AFTER THE TREATMENT WITH 1% CARRAGEENIN. | | |
| TREATMENT 1: DINAPROIC ACID 100 mg/kg os. | | |
| 1 | 100.000 | 60.000 |
| 2 | 95.000 | 70.000 |
| 3 | 95.000 | 75.000 |
| 4 | 90.000 | 65.000 |
| 5 | 105.000 | 80.000 |
| 6 | 90.000 | 70.000 |
| 7 | 75.000 | 55.000 |
| 8 | 115.000 | 65.000 |
| 9 | 90.000 | 70.000 |
| Mean | 95.000 | 67.778 |
| S.E. | 3.727 | 2.515 |
| N. | 9 | 9 |
| TREATMENT 2: IBUPROFEN 100 mg/Kg os. | | |
| 1 | 100.000 | 65.000 |
| 2 | 90.000 | 65.000 |
| 3 | 90.000 | 60.000 |
| 4 | 95.000 | 60.000 |
| 5 | 95.000 | 50.000 |
| 6 | 105.000 | 100.000 |
| 7 | 95.000 | 60.000 |
| 8 | 90.000 | 50.000 |
| 9 | 105.000 | 95.000 |
| Mean | 96.111 | 67.222 |
| S.E. | 2.003 | 6.016 |
| N. | 9 | 9 |
| RANDALL-SELITTO READING 3 HOURS AFTER THE TREATMENT WITH 1% CARRAGEENIN. | | |
| TREATMENT 1: DINAPROIC ACID 100 mg/kg os. | | |
| 1 | 100.000 | 105.000 |
| 2 | 95.000 | 95.000 |
| 3 | 95.000 | 120.000 |
| 4 | 90.000 | 110.000 |
| 5 | 105.000 | 90.000 |
| 6 | 90.000 | 80.000 |
| 7 | 75.000 | 95.000 |
| 8 | 115.000 | 80.000 |
| 9 | 90.000 | 100.000 |
| Mean | 95.000 | 97.222 |
| S.E. | 3.727 | 4.418 |
| N. | 9 | 9 |
| TREATMENT 2: IBUPROFEN 100 mg/kg os. | | |
| 1 | 100.000 | 95.000 |
| 2 | 90.000 | 110.000 |
| 3 | 90.000 | 100.000 |
| 4 | 95.000 | 90.000 |
| 5 | 95.000 | 75.000 |
| 6 | 105.000 | 120.000 |
| 7 | 95.000 | 95.000 |
| 8 | 90.000 | 100.000 |
| 9 | 105.000 | 120.000 |
| Mean | 96.111 | 100.556 |
| S.E. | 2.003 | 4.819 |
| N. | 9 | 9 |
| RANDALL-SELITTO READING 5 HOURS AFTER THE TREATMENT WITH 1% CARRAGEENIN. | | |
| TREATMENT 1: DINAPROIC ACID 100 mg/kg os. | | |
| 1 | 100.000 | 25.000 |
| 2 | 95.000 | 50.000 |
| 3 | 95.000 | 30.000 |
| 4 | 90.000 | 40.000 |
| 5 | 105.000 | 45.000 |
| 6 | 90.000 | 35.000 |

-continued

| Test n. | Normal left paw | Inflammated right paw |
|---|---|---|
| 7 | 75.000 | 50.000 |
| 8 | 115.000 | 30.000 |
| 9 | 90.000 | 30.000 |
| Mean | 95.000 | 37.222 |
| S.E. | 3.727 | 3.130 |
| N. | 9 | 9 |
| TREATMENT 2: IBUPROFEN 100 mg/kg os. | | |
| 1 | 100.000 | 45.000 |
| 2 | 90.000 | 110.000 |
| 3 | 90.000 | 45.000 |
| 4 | 95.000 | 55.000 |
| 5 | 95.000 | 35.000 |
| 6 | 105.000 | 40.000 |
| 7 | 95.000 | 35.000 |
| 8 | 90.000 | 30.000 |
| 9 | 105.000 | 30.000 |
| Mean | 96.111 | 47.222 |
| S.E. | 2.003 | 8.296 |
| N. | 9 | 9 |

The above data clearly show the effectiveness of dinaproic acid as an analgesic and antiinflammatory agent.

For the intended therapeutic uses, dinaproic acid can be conveniently formulated in pharmaceutical compositions, using conventional methods and excipients, such as those described in "Remington's Pharmaceutical Sciences Handbook", Mack Pub. Co. N.Y. USA.

In formulating the above compositions, the use of a non-toxic pharmaceutically acceptable salt of the acid of formula I may sometimes be more convenient.

Examples of said compositions comprise capsules, tablets, syrups, granulates, drops, solutions, ointments, suppositories, vials, etc.

The unit dosage will substantially depend on the conditions of the patient (weight, age and sex) and will be generally comprised from 5 to 50 mg/kg/day, in one or more administrations.

I claim:

1. A method for treating a patient suffering from pain and inflammation which comprises administering to such patient a composition comprising as the principal active ingredient a therapeutically effective amount of α-methyl-α-(3,4-dihydro-1-naphthyl)acetic acid in admixture with a pharmaceutically acceptable carrier.

* * * * *